United States Patent [19]

Murakami et al.

[11] 3,953,437
[45] Apr. 27, 1976

[54] PROCESS OF PREPARING CEPHALOSPORANIC ACID ESTER DERIVATIVES

[75] Inventors: Masuo Murakami; Kozo Takahashi, both of Tokyo; Teruaki Ozasa, Urawa, all of Japan

[73] Assignee: Yamanouchi Pharmaceutical Co., Ltd., Tokyo, Japan

[22] Filed: Mar. 8, 1974

[21] Appl. No.: 449,374

[30] Foreign Application Priority Data
Mar. 14, 1973 Japan.............................. 48-29703

[52] U.S. Cl............................................. 260/243 C
[51] Int. Cl.[2]...................................... C07D 501/04
[58] Field of Search........................ 260/243 C, 682

[56] References Cited
UNITED STATES PATENTS

| | | | |
|---|---|---|---|
| 2,237,866 | 4/1941 | Guinot | 260/682 |
| 3,641,014 | 2/1972 | Murphy | 260/243 C |
| 3,660,395 | 5/1972 | Wright | 260/243 C |
| 3,660,396 | 5/1972 | Wright | 260/243 C |

*Primary Examiner*—Nicholas S. Rizzo
*Assistant Examiner*—Mark L. Berch
*Attorney, Agent, or Firm*—Burgess, Ryan and Wayne

[57] ABSTRACT

A process of preparing a $\Delta^3$-cephalosporanic acid ester derivative which comrises reacting a cephalosporanic acid sulfoxide ester derivative with thionyl halide or a phosphorous halide.

The compounds prepared by the process of this invention are useful as intermediate compounds for preparing cephalosporin antibiotics and the compounds themselves are also potential antibacterials.

4 Claims, No Drawings

PROCESS OF PREPARING CEPHALOSPORANIC ACID ESTER DERIVATIVES

DETAILED DESCRIPTION OF THE INVENTION

The present invention relates to a process of preparing cephlosporanic acid ester derivatives and more particularly it relates to a process of preparing $\Delta^3$-cephalosporanic acid ester derivatives represented by the general formula

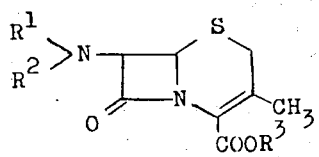   I wherein $R^1$ and $R^2$, which may be the same or different, each represents a univalent group other than a hydrogen atom, said $R^1$ and $R^2$ may be combined to form a divalent group, and $R^3$ represents an organic ester residue which can be released under mild conditions by which comprises reacting a cephalosporanic acid sulfoxide ester derivative represented by the general formula

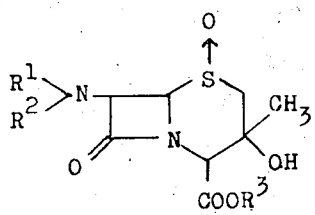   II wherein $R^1$, $R^2$, and $R^3$ have the same meaning as in general formula I, and with the halogen compound represented by a general formula

SOX$_2$   III-A or

PX$_3$   III-B wherein X represents a halogen atom.

The desired compounds of this invention are useful intermediate compounds which can be converted to cephalosporin antibiotics and when the divalent group formed by the combination of $R^1$ and $R^2$ in general formula I is, for example, a 1,1-dimethyl-3-phenyl-2-nitroso-4-oxo-2-azatetramethylene group, that is, when the desired compounds of this invention is the compounds of the formula,

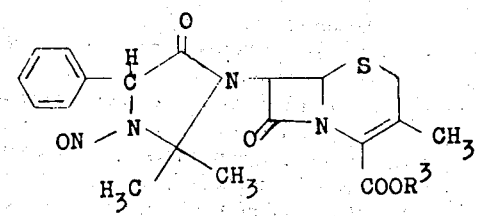

the products can be converted to cephalexin having the formula

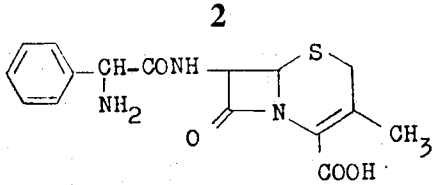

which is useful as an antibiotic by treating the compound with an acid and then water. Also the desired compounds of this invention are potential antibacterials themselves.

In the process of producing a $\Delta^3$-cephalosporanic acid or an ester thereof, a method is known in which the sulfoxide of a 7-protected amino-$\Delta^3$-cephalosporanic acid sulfoxide or an ester thereof is reduced by reacting it with phosphorus trichloride (see, Japanese Patent No. 21,111/'72).

However, it has not yet been known that the sulfoxide reduction can be similarly applied to a compound having a hydroxy group and a methyl group at the 3-position. On the other hand, it is known that when a compound which has a hydroxy group and a methyl group at the 3-position but the sulfur atom at the 1-position of which has not been oxidized reacts with thionyl chloride three kinds of compounds, that is, a compound in which the hydroxy group has been substituted by a chlorine atom and a small amount of a compound having a methyl group at the 3-position and a double bond between the 3-position and the 4-position and other compounds have been obtained (see, "Journal of the American Chemical Society"; 94(20), 7169-7170(1972)). Therefore, even if persons skilled in the art may consider that by reacting a compound having a hydroxy group and a methyl group at the 3-position and an oxidized sulfur atom at the 1-position with thionyl chloride or phosphorous trichloride, a compound having a methyl group at the 3-position and a double bond between the 3-position and the 4-position is obtained, they would as a matter of course presume that the amount of the compound that is obtained is small.

Under such a technical level, the inventors have discovered that when a starting material of formula II is caused to react with a halogen compound such as thionyl chloride (formula III-A, X is chloride) or phosphorus trichloride (formula III-B, X is chloride), a product of formula I only is obtained unexpectedly without accompanied by the formation of by-products.

That is, according to the process of this invention, the desired products of general formula I can be obtained by a quite simple manner.

As groups $R^1$ and $R^2$ of general formula II representing the starting material used in this invention, there are various groups other than hydrogen atom and specific examples of the univalent groups represented by $R^1$ and $R^2$ are a straight or branch alkyl chain or a cyclic alkyl group such as a methyl group, an isobutyl group, a cyclohexyl group, etc.; an aralkyl group such as a benzyl group, a phenethyl group, a furylethyl group, a pyridylmethyl group, etc.; a substituted alkyl group such as a trifluoromethyl group, a methoxymethyl group, a phenoxyethyl group, a benzylthioethyl group, etc.; an aryl group such as a phenyl group, a naphthyl group, a quinolyl group, a tolyl group, a p-nitrophenyl group, etc.; an acyl group such as an acetyl group, a phenylacetyl group, a cyclohexylacetyl group, a benzoyl group, an α-phenoxyacetyl group, etc.; a carbamoyl group such as an acetamido group, a N-methylbenzamido group, etc.; a dimethoxyphosphinyl group; a trimethylsilyl group; and the like. Also, specific examples of divalent groups formed by the combination of $R_1$ and $R_2$ are an arylidene group such as a salicylidene group, a benzylidene group, etc.; a phthaloyl group, a succinyl group; and the like.

Any organic ester groups which do not contribute to the reaction may be employed as the residue represented by $R^3$ of general formula II. Examples of such a group are a 2,2,2-trichloroethyl group, a triphenylmethyl group, a bis(p-methoxyphenyl)methyl group, a benzhydryl group, a phenacyl group, a p-bromophenacyl group, a 3,5-di-tert-butyl-4-hydroxybenzyl group, a phthalimidomethyl group, a benzyl group, a nitrobenzyl group, a p-toluenesulfonylethyl group, etc.

In the practice of this invention, a starting material of general formula II is dissolved or suspended in an inert solvent such as chloroform, dimethylformamide, methylene chloride, carbon tetrachloride, etc. and after cooling the solution or the suspension to a low temperature, preferably to temperatures lower than 0°C., the halogen compound represented by formula III-A or III-B is added to it in an excessive amount, preferably in an amount more than double the molar amount of the starting material.

It is desirable for the smooth progress of the reaction to add a tertiary base such as pyridine, N-methylmorpholine, N,N-dimethylaniline, triethylamine, etc., to the reaction system in an amount more than the equimolar amount of the compound of the formula III-A or III-B.

The desired product of the formula I may be isolated and purified by an ordinary chemical treatment such as extraction, concentration, column chromatography, and the like.

The following examples are intended to illustrate the process of this invention but not to limit in any way.

EXAMPLE 1

In 15 ml. of anhydrous chloroform was dissolved 500 mg. of benzhydryl 3-hydroxy-3-methyl-7-phthalimidocepham-4-carboxylate sulfoxide and after adding to the solution 558 mg. of N-methylmorpholine and 253 mg. of phosphorus trichloride successively under ice cooling, the mixture was stirred for 2 hours. The reaction mixture obtained was washed with water, dried over anhydrous magnesium sulfate, and concentrated under reduced pressure. The concentrate thus formed was subjected to a silica gel column chromatography (diameter 1.8 cm., height 12 cm.). The product was then eluted using a mixture of benzene and ethyl acetate of 9 : 1 in volume ratio as an eluant. The effluents were combined and concentrated under reduced pressure Then, by adding ether to the concentrate, 210 mg. of a white powder of benzhydryl 3-methyl-7-phthalimido -$\Delta^3$-cephem-4-carboxylate was obtained.

The chemical structure of the product estimated by infrared absorption spectra thereof coincided with the assumed chemical structure.

Nuclear magnetic resonance spectra (in $CDCl_3$): δ: 2.20 (3H, S), 2.64, 2.90, 3.55, 3.81 (A.B pattern, 2H), 4.96 (d, J = 4.5, 1H), 5.62 (d, J = 4.5, 1H), 6.85 (1H, S), 7.0–7.9 (14H).

EXAMPLE 2

A. In 20 ml. of chloroform was dissolved 620 mg. of benzhydryl 3-hydroxy-3-methyl-7-(2,2-dimethyl-3-nitroso-4-phenyl-5-oxo-1-imidazolidinyl)cepham-4-carboxylate and 10 ml. of chloroform containing 142 mg. of perbenzoic acid was added to the solution under ice cooling. After the reaction was over, the reaction mixture was concentrated under reduced pressure and the crystals of benzhydryl 3-hydroxy-3-methyl-7-(2,2-dimethyl-3-nitroso-4-phenyl-5-oxo-1-imidazolidinyl)-cepham-4-carboxylate sulfoxide thus precipitated were recovered by filtration and washed well with ether. The amount of the product obtained was 610 mg.

Infrared spectrum: 1003 cm$^{-1}$ (S O). Nuclear magnetic resonance spectra (in $D_6$-DMSO): δ: 1.09 (3H, S), 2.0 (3H, S), 2.08 (3H, S), 2.75, 2.96, 3.32, 3.53 (AB pattern, 2H), 4.40 (1H, S), 4.75 (1H, d, J = 4.5), 5.65 (1H, S), 5.72 (1H, d, J = 4.5), 6.94 (1H, S), 7.2–7.6 (16H).

(B). In 15 ml. of anhydrous dimethylformamide was suspended 500 mg. of the product obtained in Example 2-(A) and after cooling the solution to temperatures lower than −20°C., 450 μ l. of pyridine was added to the suspension. Then, after cooling the mixture to temperatures lower than −30°C., 165μl. of phosphorus trichloride was added to the mixture.

The temperature of the reaction mixture was gradually raised to 0°C. over a period of about 1 hour and then the mixture was stirred for 2 hours at room temperature. To the reaction mixture was added 50 ml. of methylene chloride and the resultant mixture was washed three times each time with 20 ml. of water. The organic solvent layer formed was separated, dried over anhydrous magnesium sulfate, and concentrated under reduced pressure. The concentrate was then subjected to a silica gel column chromatography (diameter 1.8 cm., height 10 cm.). The product was eluted using a mixture of benzene and ethyl acetate of 3 : 1 by volume ratio as an eluant. The effluents were combined, and concentrated under reduced pressure. Then, by adding ether to the concentrate, 207 mg. of the white precipitate of benzhydryl 3-methyl-7-(2,2-dimethyl-3-nitroso-4-phenyl-5-oxo-1-imidazolidinyl)-$\Delta^3$-cephem-4-carboxylate was obtained.

The chemical structure of the product estimated from the infrared absorption spectra of it coincided with the assumed chemical structure.

Nuclear magnetic resonance spectra (in $CDCl_3$): δ: 1.93 (3H, S), 1.98 (3H, S), 2.20 (3H, S), 2.49, 2.74, 3.40, 3.65 (AB pattern, 2H), 4.82 (1H, d, J = 4.2), 4.99 (1H, d, J = 4.2), 5.45 (1H, S), 6.94 (1H, S), 7.2–7.5 (15H).

EXAMPLE 3

In 20 ml. of anhydrous chloroform was suspended 1 g. of the product obtained in Example 2-(A) and then 770 mg. of pyridine and 389 mg. of thionyl chloride were added to the suspension under ice cooling. After stirring the mixture for 22 hours at room temperature the reaction mixture was washed four times each time with 30 ml. of water, dried over anhydrous magnesium sulfate, and concentrated under reduced pressure. Then, by treating the concentrate through a column chromatography as in Example 2-(B), 410 mg. of benzhydryl 3-methyl-7-(2,2-dimethyl-3-nitroso-4-phenyl-5-oxo-1-imidazolidinyl)$\Delta^3$-cephem-4-carboxylate was obtained.

What is claimed is:

1. A process of preparing a $\Delta^3$-cephalosporanic acid ester of the formula

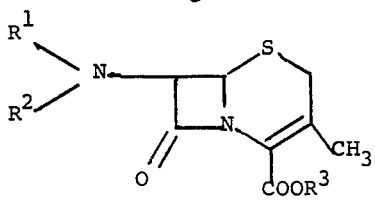

wherein $R^1$ and $R^2$ which may be the same or different, each represent a member selected from the group consisting of a straight or branched chain alkyl group of 1 to 4 carbon atoms, a cyclohexyl group, a benzyl group, a phenethyl group, a furylethyl group a pyridylmethyl group, a trifluoromethyl group, a methoxymethyl group, a phenoxyethyl group, a benzylthioethyl group, a phenyl group, a naphthyl group, a quinolyl group, a tolyl group, a nitrophenyl group, an acetyl group, a phenylacetyl group, a cyclohexylacetyl group, a benzoyl group, an alpha-phenoxyacetyl group, an acetamido group, a dimethoxy phosphinyl group and a trimethyl silyl group and $R^1$ and $R^2$ taken together forming a member selected from the group consisting of a salicylidene group and a benzylidene group, a phthaloyl group, a 1,1-dimethyl-3-phenyl-2-nitroso-4-oxo-2-azatetramethylene group and succinyl group, and $R^3$ represents a member selected from the group consisting of a 2,2,2-trichloroethyl group, a triphenylmethyl group, a bis(p-methoxyphenyl) methyl group, a benzhydryl group, a phenacyl group, a p-bromophenacyl group, a 3,5-di-tert.-butyl-4-hydroxybenzyl group, a phthalimidomethyl group, a benzyl group, a nitrobenzyl group, and a p-toluenesulfonylethyl group, comprising the steps of adding to a mixture of cephalosporanic acid sulfoxide ester of the formula:

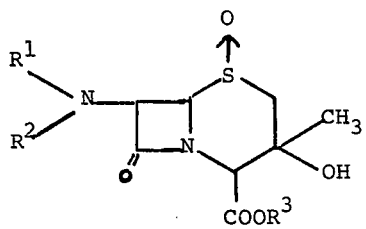

in which $R^1$, $R^2$ and $R^3$ are as defined above in an inert solvent under cooling an excessive amount of a compound of the formula $PX_3$ in which X is halogen and a more than equimolar amount with respect to $PX_3$ of a tertiary base, and recovering said $\Delta^3$-cephalosporanic acid ester.

2. The process as claimed in claim 1 wherein said reaction is conducted in the presence of an inert organic solvent.

3. The process as claimed in claim 2 wherein said inert organic solvent is chloroform, dimethylformamide, methylene chloride, or carbon tetrachloride.

4. The process as claimed in claim 1 wherein said reaction is conducted under cooling to temperatures lower than 0°C.

* * * * *